United States Patent [19]

Mattoon et al.

[11] Patent Number: 5,824,511
[45] Date of Patent: Oct. 20, 1998

[54] METHOD FOR ENHANCING THE PRODUCTION OF HEMOPROTEINS

[75] Inventors: James R. Mattoon; George Bajszár, both of Colorado Springs, Colo.

[73] Assignee: University Technology Corporation, Boulder, Colo.

[21] Appl. No.: 509,951

[22] Filed: Aug. 1, 1995

[51] Int. Cl.$^6$ ..................................................... C12P 21/06
[52] U.S. Cl. ........................ 435/69.6; 435/70.1; 435/69.1
[58] Field of Search .................................. 435/69.1, 69.6, 435/70.1, 71.1, 71.2

[56] References Cited

U.S. PATENT DOCUMENTS

| | | | |
|---|---|---|---|
| 4,849,348 | 7/1989 | Marcker et al. | 435/69.1 |
| 4,902,620 | 2/1990 | Bard et al. | 435/172.3 |
| 5,049,493 | 9/1991 | Khosla et al. | 435/69.1 |
| 5,242,892 | 9/1993 | Rebeiz | 504/129 |
| 5,635,375 | 6/1997 | Kraus et al. | 435/71.1 |

FOREIGN PATENT DOCUMENTS

| | | |
|---|---|---|
| WO 90/13645 | 11/1990 | WIPO . |
| WO 92/16634 | 10/1992 | WIPO . |

OTHER PUBLICATIONS

Adachi et al., Oxygen Binding and Other Physical Properties of Human Hemoglobin Made in Yeast, *Protein Engineering*, vol. 5, No. 8, pp. 807–810, 1992.
Borralho et al., In Situ Assay for 5–Aminolevulinate Dehydratase and Application to the Study of a Carbolite Repression–Resistant *Sacchromyces cerevisiae* Mutant *Journal of Bacteriology*, Oct., 1983, pp. 141–147, vol. 156, No. 1.
Borralho et al., "Parallel Changes in Catabolite Repression of Haem Biosynthesis and Cytochromes in Repression–resistant Mutants of *Saccharomyces cerevisiae*", *Journal of Gen. Microbiology*, vol. 13, pp, 1217–1227, 1989.
Borralho et al. "Purification of δ–Aminolevulinate Dehydratase from Genetically Engineered Yeast", *Yeast*, vol. 6: 319–330 (1990).
Carvajal, "Isolation and Characterization of a New Mutant of *Saccharomyces cerevisiae* with Altered Synthesis of 5–Aminolevulinic Acid", *Journal of Bacteriology*, Jun., 1990, pp. 2855–2861, vol. 172, No. 6.
Coghlin et al. "Structural and Functional Characterisation of Recombinant Human Haemoglobin A Expressed in *Saccharomyces cerevisiac*," *European Journal of Biochemistry*, vol. 207, pp. 931–993, 1992.
De Llano et al., "Recombinant Human Sickle Hemoglobin Expressed in Yeast", *Proc. Natl. Acad. Sci. USA*, vol. 90, pp. 918–922, Feb., 1993.
Grandchamp et al., "Enzymes of the Name Biosynthesis Pathway: Recent Addresses in Molecular Genetics", *Seminars in Hematology*, vol. 25, No. 4, pp. 303–311, Oct., 1988.
Mattoon, et al., "Coordinate Regulation of Mitochondrial Cytochrome Formation in *Saccharomyces cerevisiae*" *Genetics of Respriratory Enzymes in Yeasts* (Materials of the International Conference Karpacz in 1990), pp. 15–22.
Mattoon, "Molecular Genetics of Heme and Cytochrome Biosynthesis", *Anal. Acad. Nac. Cs. Ex. Fis. Nat.*, Buenos Aires, tomo. 40, 1988, pp. 87–94.
Meussdorfer et al., Effect of Mitochondrial Cytochromes and Home Content on Cytochrome P450 in *Saccharomyces cerevisiae*, *Journal of General Microbiology* vol. 132, pp. 2187–2193, 1986.
Myers et al., "Characterization of the Yeast HEM2 Gene and Transcriptional Regulation of COX5 and COR1 by Heme", *The Journal of Biological Chemistry*, vol. 262, No. 35, pp. 16822–16828, December Issue, 1987.
Oechsner et al., Expression of Yeast Cytochrome c$^1$ is Controlled at the Transcriptional Level by Glucose, Oxygen and Haem, *Mol. Gen. Genet.*, 192, pp. 447–459.
Ogden et al., Expression and Assembly of Functional Human Hemoglobin in *S. Cerevisiae*, *Biomat., Art, Cells & Immob. Biotech*, 20 (2–4) pp. 473–475 (1992).
Schauer et al., Heterologous Expression of Human 5–Aminolevulinate Dehydratase in *Saccharomyces cerevisiae*, *Current Genetics*, vol. 17, pp. 106, 190.
Wagenbach et al., Synthesis of Wild Type and Mutant Hman Hemoglobins in *Saccharomyces Cerevisiae*, *Biotechnology*, vol. 9, pp. 57–61, Jan., 1991.

*Primary Examiner*—Terry A. McKelvey
*Attorney, Agent, or Firm*—Sheridan Ross P.C.

[57] ABSTRACT

A method for increasing the production of desired hemoproteins is described in which the rate-limiting step in a heme biosynthetic pathway is deregulated to increase the quantity of the rate-limiting enzyme. In yeast, transforming cells with the HEM2 gene increases the quantity of the rate-limiting enzyme ALA dehydratase. Free heme concentrations are reduced in cells by providing heme binding agents that complexes with overproduced heme, thereby reducing or eliminating heme feedback inhibition in the cell. The present invention permits investigation of other factors effecting the heme biosynthetic pathway by reducing interference from heme feedback inhibition within that pathway.

16 Claims, 7 Drawing Sheets

```
HAP2/3/4
GGATCCAATCATTCCTGTTCGATAATCTCAAAGGGACATTCCCCCTCTGGAGAGAAATTAGTGACAAAGCTGTGGTCAGTTGGATAAGAGTTCTCTTGTAC    -1791
    BamHI
CCCTTGTGACGAGAATAAAATAACAAAAAAAATGCAAACAGCAAACGACAAGCACAAGCACAATAGCTTATAAGGCCATTCCTAGCAATTTTCGGAA        -1691

GAATGGCTATACCCAAATACAGATTTGGCGACAGTTTACACATGGAGATGCGACATCGTGCTCTATTGGATAAGTCAAATCATCCCTATTATCTATC         -1591

CCTGTCATATGCTGCGAGTATCCGTTAAAGTCAACCTGTGCATTCTTTGCTGACATTCAGTATACCATCAGTGTCTGCACATGAACCGGA                -1491
        Xcal
TTCCGTCATAAACATTTATCTGCCCTTTCCAGTCATTGTTCCTGACAGAGAAACTGTCCCTCTGTTTACATTTATGACAGTGTCTGCACATGAACCGGA       -1391
HAP1
ATCCATACGGGTGAAATTAGTTGAGAGTGTATAGCCATTAACACCATCAAAAATTTACTTCCGCATAACCATCTCCTGCTCCCATAGATACAGGATTGAAC    -1291

TGTCATGTGCAGAGATCGACACTCGTCAGTATCAACTCTACGCGCCACTGTGTAAATCATTAGAAATGTAACCAGGTTCCGTGAGATTCTTATATATGACT    -1191
                        HAP2/3/4
ACGAGACAGTGCTTTCAGACGCAAAGTCTAACCATCCTTGAAAACGTCTTCCAATCATGAAAATTAAAACTCACGGCTCTATATTTTCACGTCGAGCTTCA    -1091

TTTTGGGCCACTATTAGATCCTGTGTTTTATTCCAAGGTGTATTGTCATATTTAATCTTGAAAATAATTTCTAATCTGTGTGATTATTACAGTAGATTC       -991

TATTGAAAGGACACCTACAAGCTCATAGAGTCCGGTGTACTGGCACAGAACACAGATGACAATACAAAAGTAAATAAATCTATGACAGCAATTCCTATT      -891

TTCTTTTACATTTATATTGATTAGCTTACGATTTCTGTATTTATAGAGCGTGTAGTTACATATCCAGATACCTGTCTCTTCTAGGTGAACAGTTGGTTTCAG   -791

TCAAAAATTATTATTACGGATTCTTGGACGGTAGCTTCCCTGCCTGACGGGGGTGCATGATTCCACTCTTTCGGGAACAATGATAATTATTGTTAGTTTTGATTATGCT -691

TAATCTTAATTCGCACATGGAATGCCTGCATTGTCACGAGAACATTGAAACATATACAAAAAACAAATTTGAAATGAAAACAAAGCAATTTACAGAAAT      -591
                                                                                YAP1
GACTGCCTGGTGCTAATTCTTGCATATATTTTATTTTAATTAACTAGAAATCAGCGTCAATTATAGTTTCTGGTGAGTCAGCCAATGTCTGTAAATAAA      -491
                                        PacI
                                            (CREB)
AACAATATGCTTAAGAGGATTAACAGTGGCACAAGAGGCAAAGAGAGGAAGAAGGCGTACACGTCACATGAATATATAAAAGGAGTGTTACTATCAATT      -391
    AflIII                                                                                  MunI
GGACCATCTTCGACGTTTCTATCTGCTACAAGCCTGTGTCGCCGAATTACTTTATTGGGTCTTGTTATATACGCCGAAATACATCATCCAAGATGA        -291

CGATAAAATCATCCAAAAATTGTTGCCGAAAAAAAATTGGAAAAGGTGAAAAAAAAAATCAAAATACGGGTAAACGAGCAATCCCTGTTCGGTGCGGTG      -191
                                                                    REB1
HAP2/3/4
ATTGGCTTGAGGCAAGCTTCCCGCTTGATTTATATATAAGAGTAAGGCAACCTAATAAATGCTAGCAACATCTATCGCCCACTCTATTGTCTTTGATTTCT    -91
            HindIII                                                            NheI
HAP/2/3/4
TGCCCAATCAGCCAAATAAAAAAAGTTTACTGCTTACTCATATTATTGCTTACTCCAGTAATTCATACCTAGAAATTGACAAAACC atg cat
                                                                                         NsiI
```

METHOD FOR ENHANCING THE PRODUCTION OF HEMOPROTEINS

FIELD OF THE INVENTION

The present invention is directed to a method to improve the production of cytoplasmic hemoproteins and is more particularly directed to a method to increase the production of homologous and heterologous hemoproteins in yeast cells by increasing the production of the HEM2 gene product in the heme biosynthetic pathway.

BACKGROUND OF THE INVENTION

An important class of homologous and heterologous proteins produced in genetically engineered cells is represented by proteins carrying a heme prosthetic group. A number of heme proteins are of great importance from a pharmaceutical point of view. Many commercial ventures are working to enhance the biosynthesis of the heme protein family and efforts are continuing in the development of new strains of improved biochemical and cell-physiological characteristics in yeast, as well as in bacteria and fungi.

There is considerable current interest in the potential of cell-free hemoglobin as a substitute for red cells in oxygen delivery, such interest increased due to concern over viral contamination of donated blood. Recombinant DNA techniques now make it possible to produce recombinant hemoglobin in genetically engineered microorganisms, thus insuring a source of hemoglobin which is free of human blood derived infectious agents, such as hepatitis B and HIV. Methods using *E. coli* to produce human hemoglobin have been developed, however, production of hemoglobin in this way has proved to be inefficient. The removal of endotoxin from *E. coli* products is very costly. Yeast strains have also been used to produce hemoproteins, but production of such hemoproteins has proven difficult due to the lack of simultaneously abundant amounts of both apoproteins and heme in such production systems.

Heme is an essential co-factor in a large variety of enzymes and other hemoproteins, such as hemoglobin, cytochromes and myoglobin. Heme is utilized as the prosthetic group of respiratory cytochromes and cytochromes required for biosynthesis of unsaturated fatty acids, as well as in cytochrome P-450 and is utilized in sterol biosynthesis. In yeast, heme plays an important regulatory role in biogenesis of the respiratory chain enzymes, is required for assembly of cytochrome oxidase and is specifically required for transcription of the gene encoding apo-iso-1-cytochrome C. Heme is synthesized in yeast in the mitochondria in a tightly regulated fashion involving both positive and negative regulatory elements that respond to heme concentration, oxygen supply and carbon source. It functions as a co-factor in mediated transcriptional regulation of yeast respiratory genes. It is known that identified enzymes in the heme biosynthetic pathway can be manipulated to affect heme production, such enzymes including ALA synthase (encoded by HEM1), ALA dehydratase (encoded by HEM2), and PBG deaminase (encoded by HEM3).

A significant problem experienced by present researchers is that the overproduction of hemoproteins is limited due to feedback inhibition caused by excess amounts of heme within a cell. Efforts to overproduce one or more of the components ultimately desired to generate functional hemoproteins are stymied by heme feedback inhibitory responses of cells. As such, it would be desirable to resolve the long-felt, but unsatisfied need for a method that can significantly alleviate intercellular free heme concentrations so as to achieve desired production levels of hemoproteins. Moreover, it would be desirable to have a method in which the heme biosynthetic pathway can be regulated in such a manner that other critical factors in such pathway can be further studied and regulated in order to achieve greater production of hemoproteins.

SUMMARY OF THE INVENTION

One embodiment of the present invention is directed to a method to produce hemoproteins by transforming a host cell with a nucleic acid sequence encoding a rate-limiting enzyme in a heme biosynthetic pathway. The host cell is cultured under conditions effective to provide expression of the sequence to produce desired concentrations of heme. A sufficient amount of a heme binding agent capable of complexing free heme produced by the cell is supplied to reduce the concentration of free heme within the cell. The coordination of gene expression of a rate-limiting enzyme, coupled with the expression of a gene encoding a heme-binding agent, prevents undesired feedback inhibition that would otherwise be caused by excess concentrations of free heme in the cell. As described in greater detail herein, simultaneous production of heme and heme binding agents, (e.g., apoproteins) allows one to study various aspects of heme regulation, which can then be manipulated to produce further improvements in hemoprotein production systems.

In yeast, the rate-limiting enzyme is encoded in the HEM2 gene and thus, one embodiment of the present invention involves the transformation of a yeast cell with the HEM2 gene to overproduce ALA dehydratase. Preferred yeast strains include Pichia, Hansenula and strains of *S. cerevisiae*. Other host cells, such as Filamentous fungus, specifically Aspergillus and Neurospora, can also be used as suitable host cells. Using the present method, desired hemoproteins, such as hemoglobin, myoglobin and certain cytochromes, including cytochrome P450, and enzymes such as catalases and peroxidases, can be produced in unprecedented quantities, typically up to about 20% more, and in some cases up to about 40% more, than can otherwise be produced in unmodified hemoprotein-producing cells.

Transformation of suitable host cells can be accomplished using vectors of the present invention, which include multicopy plasmids or integrating vectors, such vectors controllable by inducible or constitutive promoters. Vectors of the present invention can therefore comprise gene expression cassettes for use in transforming desired host cells. In one embodiment, a vector comprises a HEM2 expression cassette operatively associated with a constitutive yeast promoter. Vectors can further include genes encoding heme binding agents to address the reduction of free heme concentrations within transformed cells. Heme binding agents of the present invention can include particular proteins or enzymes, such as apoproteins (e.g., globin), catalase T, etc. and can therefore comprise heme binding proteins involved in the production of hemoglobin, myoglobin and various cytochromes.

Another aspect of the present invention relates to recombinant cells having at least one gene encoding a rate-limiting enzyme, such cell exhibiting enhanced production of hemoproteins. Such cells can also comprise a gene encoding a heme binding agent that when expressed, is capable of reducing the concentration of free heme in the cell.

BRIEF DESCRIPTION OF THE DRAWINGS

FIG. 3 shows the nucleic acid sequence of the HEM2 promoter.

DETAILED DESCRIPTION OF THE INVENTION

Figure 1:
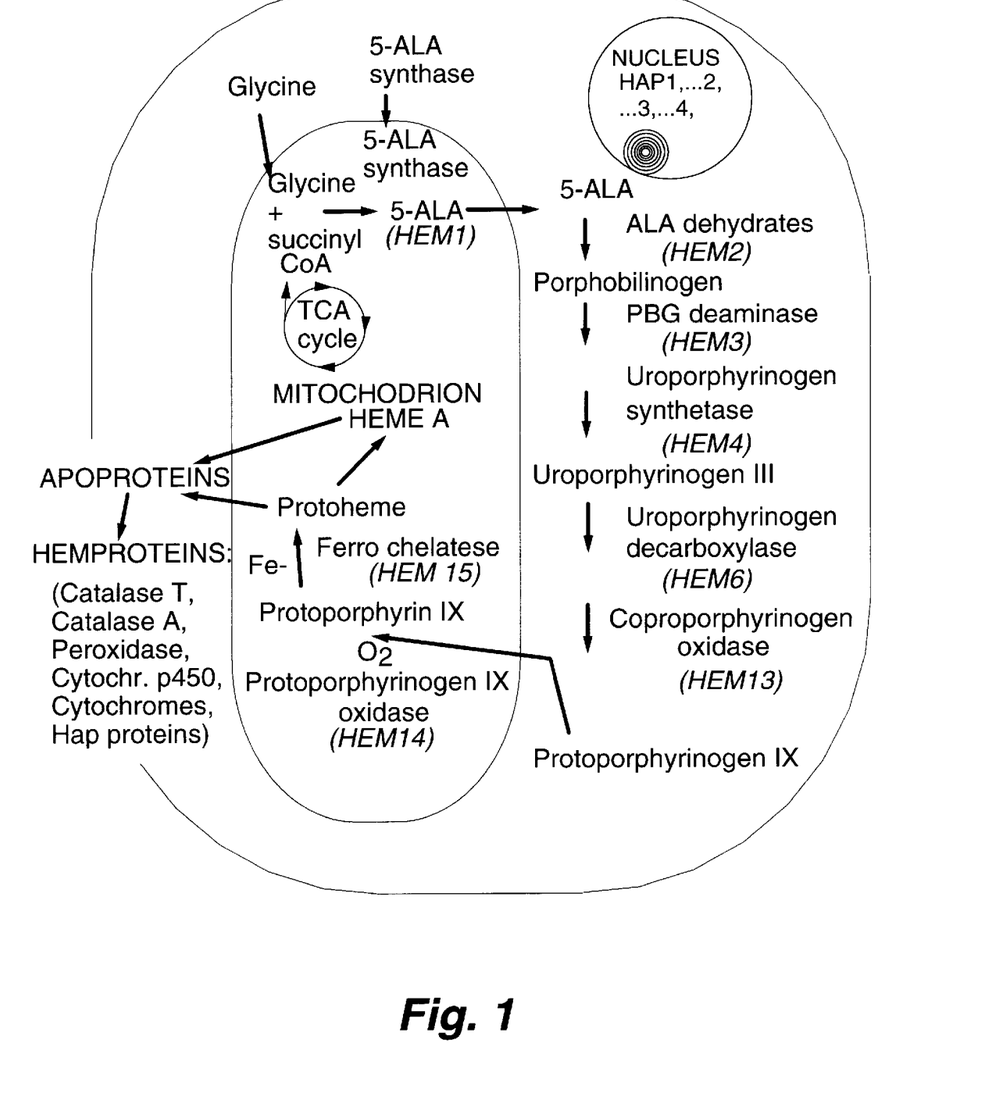
FIG. 1 shows the different products and enzymes in the heme/hemoprotein biosynthetic pathway in mitochondria and cytosol.

For efficient industrial production of hemoproteins, appropriate ratios of heme and apoproteins must be simultaneously produced in a host cell. Elimination of the rate-limiting step or steps in the heme biosynthetic pathway can be achieved by over expressing genes encoding rate-limiting enzymes involved in such pathway. The different products and enzymes in the heme/hemoprotein biosynthetic pathway in mitochondria and the cytosol is depicted in FIG. 1. By removing the rate-limiting step or steps in such pathway, overexpression of heme can be achieved. However, increased concentrations of free heme within a cell invariably leads to feedback inhibition of various components in the biosynthetic pathway. The present invention is directed to a method for enhancing the production of hemoproteins by increasing the production of heme by eliminating the rate-limiting step or steps in the heme biosynthetic pathway, and, in addition, reducing the concentration of free heme within the cell by "trapping" such heme using the ability of apoproteins to complex with such heme, thereby reducing the occurrence of heme-feedback inhibition. In such a manner, increased production of hemoproteins can be achieved. As demonstrated using apocatalase in an exemplary model system, overexpressed heme is trapped by apocatalase (a heme-binding agent) to form catalase, such expression of heme and apocatalase coordinated to optimize the production of catalase. Coordinated expression of other apoproteins and heme can similarly be used to reduce the occurrence of heme feedback inhibition, thus permitting investigations into how to define and optimize systems related to the production of desired hemoproteins.

Figure 4:
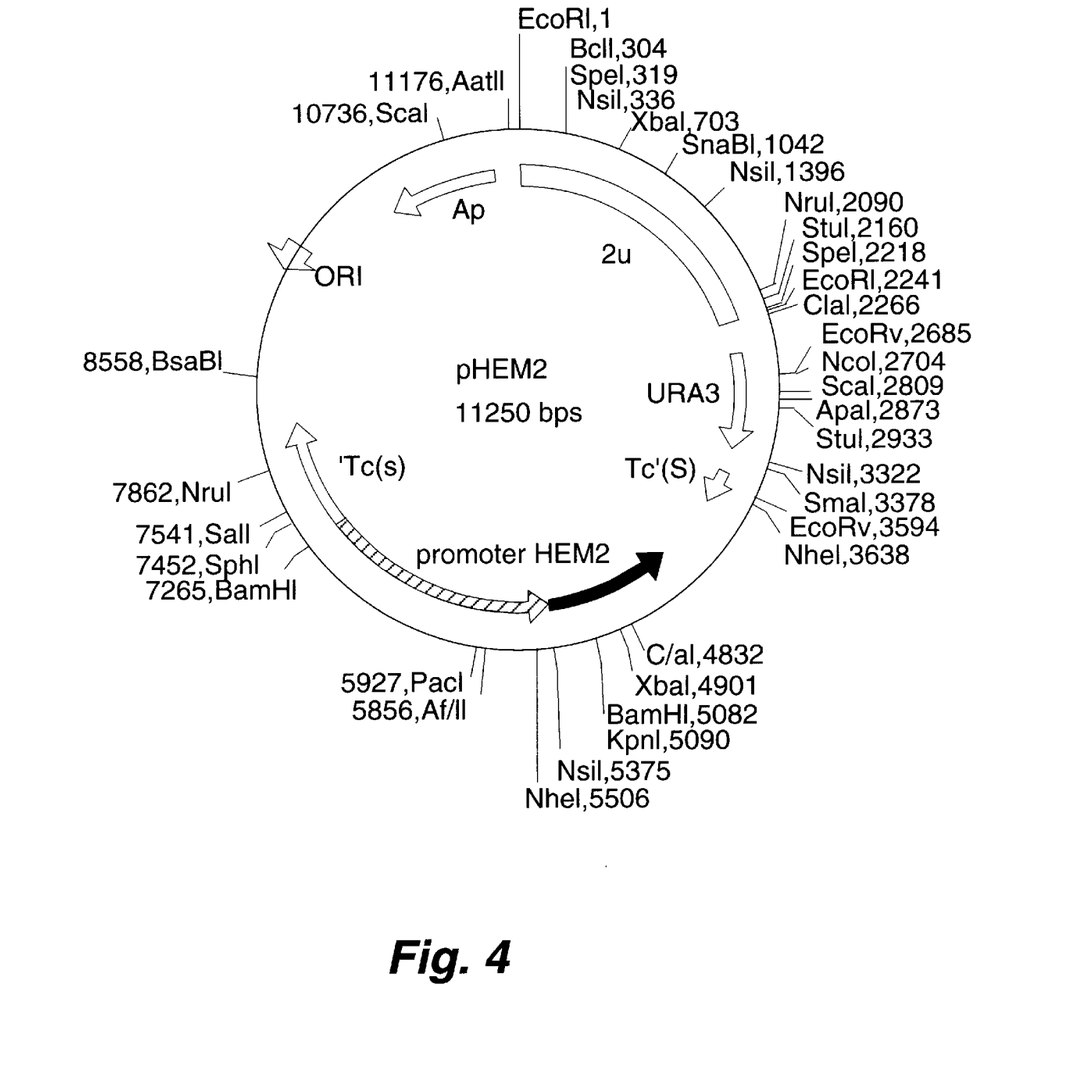
FIG. 4 shows a restriction map of a yeast plasmid for the overexpression of the HEM2 gene.

The present inventors have shown that the production in yeast of enhanced levels of intracellular heme can be mediated by increasing the production of ALA dehydratase (referred to as 5-aminolevulinic acid dehydratase or porphobilnogen (PBG) synthase), the second enzyme of the heme biosynthetic pathway, encoded by the gene HEM2. FIG. 4 shows a restriction map of a yeast plasmid for the overexpression of the HEM2 gene. The expression of HEM2 is partially repressed by glucose and, under various physiological conditions, is apparently regulated by complex, yet uncharacterized, mechanisms. To produce sufficient amounts of ALA dehydratase, the nucleic acid sequence for ALA dehydratase is used to transform cells using a suitable vector, such as a multicopy plasmid (e.g., pHEM2) or integrating vector, so that the production of ALA dehydratase is non-limiting. As described in greater detail below, the effect of HEM2 over-expression in yeast transformed with multicopy vectors is capable of being indirectly assayed using the heme dependent activity of the simultaneously over-expressed cytoplasmic catalase T enzyme. Enhancement of HEM2 gene expression results in increased cytochrome production (mediated by AMP), and, consequently, in improved fermentation characteristics of engineered yeast strains.

Using the present invention, increased amounts of hemoproteins, and particularly hemoglobins and cytochromes, can be produced, such desired amounts exceeding current production levels of existing strains by up to about 20%, and even as high as about 40%.

Figure 5:
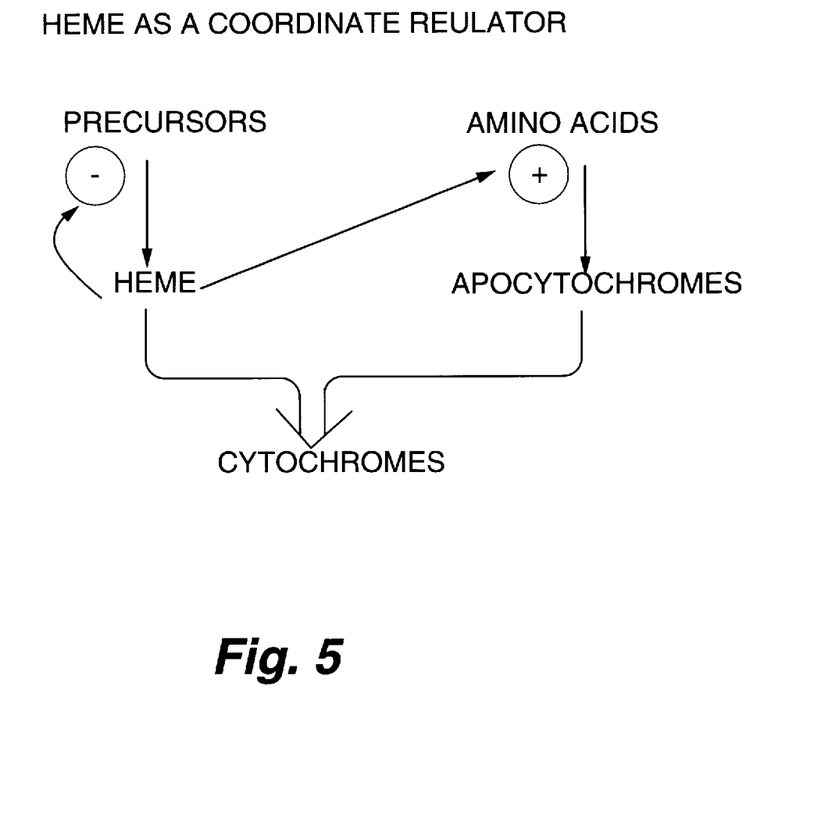
FIG. 5 is a simplified model of coordinate regulation of cytochrome biosynthesis in yeast.

Cytochromes are heme proteins localized in the mitochondria and the endoplasmic reticulum (ER). Cytochromes P450 constitute an enzyme family comprising heme proteins (e.g., $b_5$ and P450 in the ER) which function as terminal oxidases in a variety of biotransformation systems. Cytochromes P450 are used by most organisms in the metabolism of endogenous as well as xenobiotic hydrophobic compounds. A simplified model of coordinate regulation of cytochrome biosynthesis in yeast is shown in FIG. 5.

Catalases are enzymes that function outside of the mitochondria and are, together with peroxidases and superoxide dismutase, involved in the detoxification of hydrogen peroxide and superoxide radicals formed during respiration. Catalases thus act to protect cells from oxidative damage and aid in the metabolism of unusual substrates.

A number of host cells are suitable for use in the present invention, such host cells including, but not limited to, mammalian, insect, avian, reptilian, amphibian, yeast, bacterial and fungi. Preferred host cells are eukaryotic and even more preferred host cells include yeast and fungi that are known to be efficient producers of hemoproteins. In particular, yeast of the genus Pichia, and even more preferably, *Pichia pastoris*, are desirable for use in the present method. Other yeasts suitable for the present invention include *Hansenula polymorpha*. Filamentous fungis can also be used as host cells in the present invention, with a preferred genus being Aspergillus or Neurospora strains.

As used herein, transfection includes any means for introducing a nucleic acid sequence or expression vector into a host cell, including, but not limited to, transformation (e.g., with DNA coated microbeads), electroporation, microinjection, absorption, and protoplast fusion. Preferred transfection techniques involve expression of a vector, such as a multi-copy plasmid or the use of a vector that integrates into the genum of the host cell.

After transfection, transfected cells are cultured in an effective medium, which can be any medium in which the transfected cells can grow and proliferate while at the same time expressing the transfected nucleic acid sequences. An effective medium is typically an aqueous medium comprising assimilable carbohydrate, nitrogen and phosphate sources, as well as appropriate salts, minerals, metals and other nutrients, such as vitamins, growth factors and hormones. Culturing is carried out at a temperature, pH and oxygen content appropriate for the particular transfected cell, such culturing conditions well within the expertise of one of ordinary skill in the art.

The expression vectors suitable for use with the present invention may be any vector which may conveniently be subjected to recombinant DNA procedures, and the choice of vector will often depend on the host cell into which it is to be introduced. Thus, the vector may be an autonomously replicating vector which exists as an extrachromosomal entity, the replication of which is independent of chromosomal replication, such as a plasmid. Alternatively, a vector may be one in which, when introduced into a host cell, is integrated into the host cell genome and replicated together with the chromosomes into which it has been integrated. Expression vectors of the present invention should be operatively connected to a suitable promoter (e.g., conditional promoters), being any DNA sequence which shows transcriptional activity in the host cell of choice, and may be derived from genes encoding proteins either homologous or heterologous to the host cell.

In accordance with one embodiment of the present invention, a nucleic acid sequence encoding for a rate-limiting enzyme in the heme biosynthetic pathway is isolated and used to transform a suitable host cell. A nucleic acid molecule can be DNA, RNA, or hybrids or derivatives of either DNA or RNA. Nucleic acid molecules of the present invention can include regulatory regions that control expression of the nucleic acid molecule (e.g., transcription or translation control regions), full-length or partial coding regions, and combinations thereof. Any portion of a nucleic acid molecule of the present invention can be produced by: (1) isolating the molecule from its natural milieu; (2) using recombinant DNA technology (e.g., PCR amplification, cloning); or (3) using chemical synthesis methods. A nucleic acid of the present invention can include functional equivalents of natural nucleic acid molecules encoding desired apoproteins, apocytochromes and desired enzymes involved in the heme biosynthetic pathway, including natural allelic variants and modified nucleic acid molecules in which nucleotides have been inserted, deleted, substituted, and/or inverted in such a manner that such modifications do not substantially interfere with the nucleic acid molecule's ability to encode such components.

A particular host can be cultured under conditions effective to provide expression of the desired sequence for a rate-limiting enzyme. A sufficient amount of a "heme-binding agent" is then supplied to the host cell. For example, the heme-binding agent can be supplied to the host cell by transforming the host cell with such heme binding agent. In one embodiment, host cells can be transformed with a gene-encoding a desired apoprotein which, upon expression, will act to bind free heme within the cell, thus forming hemoproteins. Both the nucleic acid sequence encoding the rate-limiting enzyme as well as the heme-binding agent can be present on one expression vector or, alternatively, can be on separate vectors, such as separate multi-copy plasmids. Techniques for isolating nucleic acid sequences and expression vectors and for operatively linking a coding sequence to an expression vector are described in detail in Sambrook et al., *Molecular Cloning: A Laboratory Manual,* Coldspring Harbor Labs Press, 1989. Effective expression systems can be constructed from any control elements, typically being control sequences from a species compatible with a host cell, including but not limited to promoters, operators, enhancers, ribosome binding sites and Shine-Delgarno sequences. Such control elements are operatively linked to the nucleic acid sequences of the present invention, described herein, using methods known to those of skill in the art (see, for example, Sambrook et al., ibid.)

Use of high yield promoters, such as ADH, enolase, etc. or the tryptophan (TRP) promoter/operator system, can also be used. Other inducible and constitutive promoters may be used to coordinate synthesis of desired apochytochromes, apoproteins, and iron-porphyrin prosthetic groups.

In one embodiment of the invention, the method includes accumulation of desired numbers of host cells, after which time suitable expression of either a heme-binding agent (e.g., an apoprotein) or a rate-limiting enzyme is induced so as to produce the maximum amount of hemoproteins from the cells. It is preferable to have an adequate supply of heme present while a cell is expressing a particular apoprotein, so as to provide an adequate amount of the constituents required to form desired hemoproteins, thereby ending up with purer materials that do not require expensive and time intensive purification processes.

One aspect of the present invention therefore involves the use of yeast transformed with particular genes encoding enzymes that are involved in the production of heme proteins. Yeast cells enriched in the first enzyme of heme and porphyrin biosynthesis (e.g., 5-aminolevulinate synthase or ALA synthase) can be obtained by transforming yeast cells with the HEM1 gene, which encodes ALA synthase. ALA synthase is located in the mitochondrial matrix. Appropriate amounts of ALA are required to provide excess precursor for porphyrin and heme biosynthesis. This can be accomplished by rendering ALA synthase non-limiting for heme production by replacing the normal promoter for HEM1 with either an inducible promotor or a constitutive promoter, such as TRP1p or glyceraldehyde-3-phosphate dehydrogenase (GAPDH). Under these more powerful promoters, HEM1 is introduced into cells, either on an episomal plasmid or on an integrating vector, so that the production of ALA synthase is increased.

In order to efficiently make certain hemoproteins, for example, cytochromes, two processes must be regulated coordinately: (1) the biosynthesis of heme; and (2) the biosynthesis of the specific apoproteins of the cytochromes or other hemoproteins. Contrary to conventional belief, (see Coghlan, European Journal of Biochemistry, 207, 931, 935, 1992), the present inventors have discovered that endogenous heme synthesis is not capable of supporting the production of high levels of many heterologous heme proteins. These two processes are normally coordinated in the cell so that neither excess heme nor excess apocytochrome accumulates. It is known, however, that heme exerts negative feedback control on its own synthesis and positive control on the synthesis of at least some apocytochromes. As yeast grows on a glucose medium, the relative activities of the first two enzymes in the heme biosynthetic pathway change, causing the intracellular concentration of the intermediate 5-aminolevulinate (5-ALA) to change with time. The present inventors have discovered that the second enzyme in the yeast heme biosynthetic pathway is the primary rate limiting enzyme. By transforming cells with a HEM2-containing plasmid, the present inventors are able to ultimately increase the amount of PBG synthase in the cell, and thus the production of heme, to increase the production of hemoproteins such as hemoglobin, myoglobin, various cytochromes and hemoprotein enzymes such as catalase. By doing so, the normal rate limiting step in the pathway at the second enzyme is shifted back to the first enzyme. For example, in the yeast heme pathway between 5-aminolevulinate and uroporphyrinogen, the rate limiting enzyme is PBG synthase. When excess PBG synthase is introduced into a cell by transformation with, for example, a multicopy plasmid bearing the HEM2 gene, ALA synthase becomes the rate limiting enzyme. Similar transformation of cells to achieve the overexpression of HEM1 can then be performed to further adjust the production of desired hemoproteins.

For the expression of recombinant hemoglobin in yeast, such as *S. cerevisiae,* Pichia and Hansenula, plasmids containing alpha-globin and beta-globin cDNA can be used to transform such yeast cells. One of skill in the art will appreciate DNA manipulation techniques to achieve such transformation following standard protocols (e.g., Sambrook et al., 1989) and yeast formation has been previously described (e.g., Hinnen et al., 1978). Yeast strains can be grown, for example, in shaken flasks in defined minimal medium comprising 0.67% yeast nitrogen base without amino acids (DIFCO with 2% sucrose as a carbon source, or alternatively, in FED-batch fermentation in Dw medium) (see e.g., Fiechter et al., 1981). The production of recombinant hemoglobin in yeast requires the coexpression of alpha-globin and beta-globin sub-units within the same cell, resulting in the synthesis of the globin proteins and assembly with heme components, into fully functional tetrameric hemoglobin. Various culturing techniques for yeast are known to those of skill in the art (see e.g., Borralho, et al., Yeast, Vol. 6: 319–330, 1990), (Oechsner, et al., Mol. Gen. Genet, 232: 447–459, 1992). Similarly, purification and recovery techniques for particular heme proteins are known by those in the art. Id. Recombinant hemoglobin produced in certain yeast strains, for example, S. cerevisiae, is able to incorporate heme produced by the yeast heme synthetic pathway. Growth under conditions that favor heme synthesis (aerobic conditions with a non-fermentable carbon source) favors the production of hemoglobin with a full complement of heme.

One embodiment of the present invention directed to the overproduction of cytoplasmic hemoproteins is exemplified by the increased production of yeast catalase T. As will be appreciated by one skilled in the art, the following explanation relating to the production of catalase T serves as a model for producing other hemoproteins, such as hemoglobin, myoglobin and various cytochromes in heretofore unprecedented amounts. The present inventors have discovered that when apocatalase is overproduced, yeast heme synthesis regulation does not increase beyond a certain point on its own to meet the increased demand for heme.

The present investigators have performed studies on the effect of HEM2 over-expression on the production of catalase T reporter enzyme. Catalase T is a cytoplasmic hemoprotein, encoded by catalase T gene, CTT1, that catalyzes the degradation of hydrogen peroxide. It can be used as a reporter enzyme to test the effect of over-expression of heme biosynthetic enzymes on hemoprotein production. Catalase T expression can be tested using $H_2O_2$-agar overlay and visual monitoring of oxygen bubbles trapped within an agar overlay around yeast transformant colonies. The HEM2 over-expression system described above, when used in combination with hemoglobin expression plasmids, can be used to increase the production of hemoglobin and globin expression plasmids can be used for this purpose.

Figure 2:
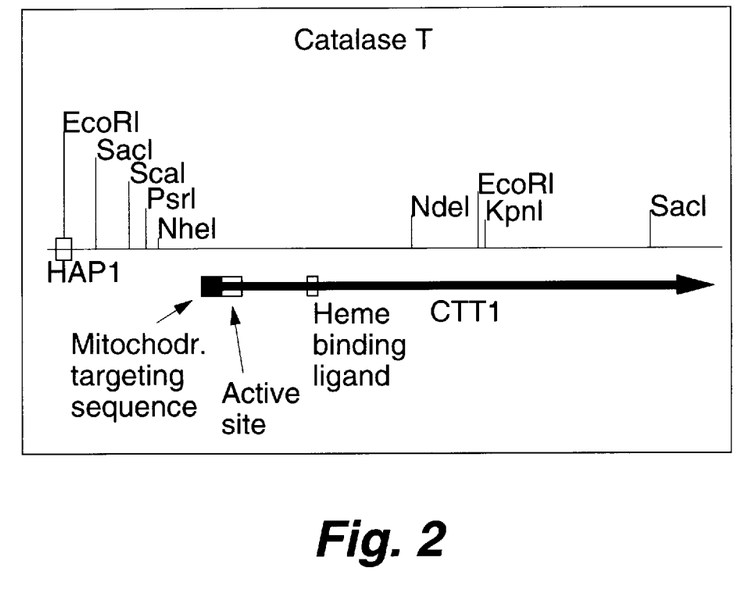
FIG. 2 shows a restriction and functional map of the catalase T gene and its product.
Figure 6A:
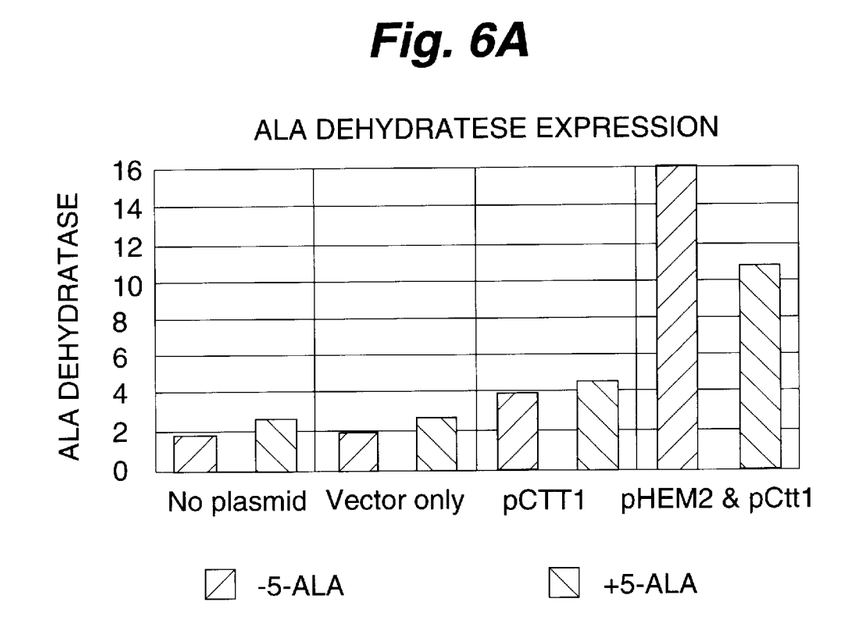
FIG. 6 shows the results of 5-ALA dehydratase and catalase assays in double transformant yeast cells simultaneously harboring the multicopy plasmids pctt1+pHEM2.
Figure 6B:
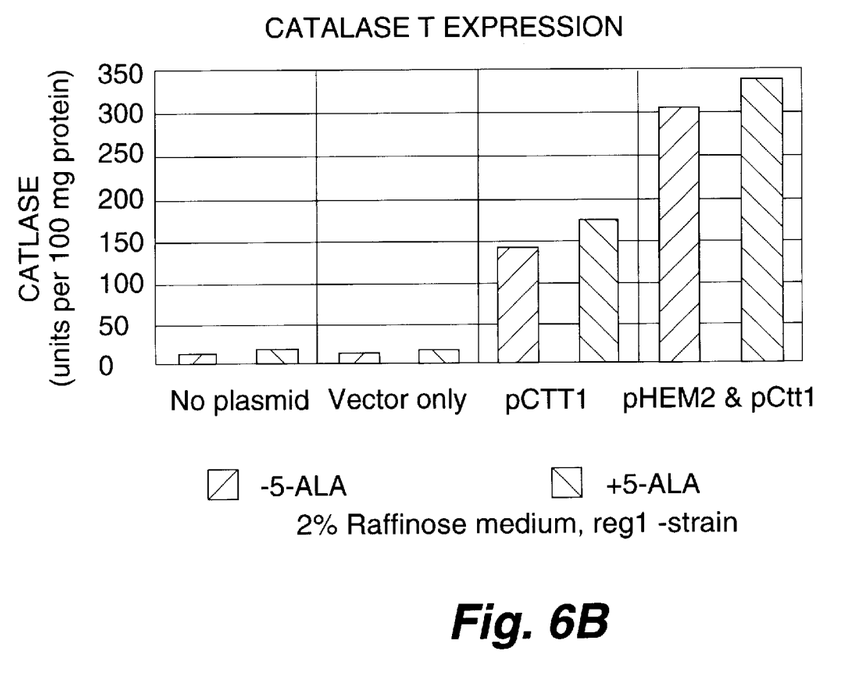
Figure 7:
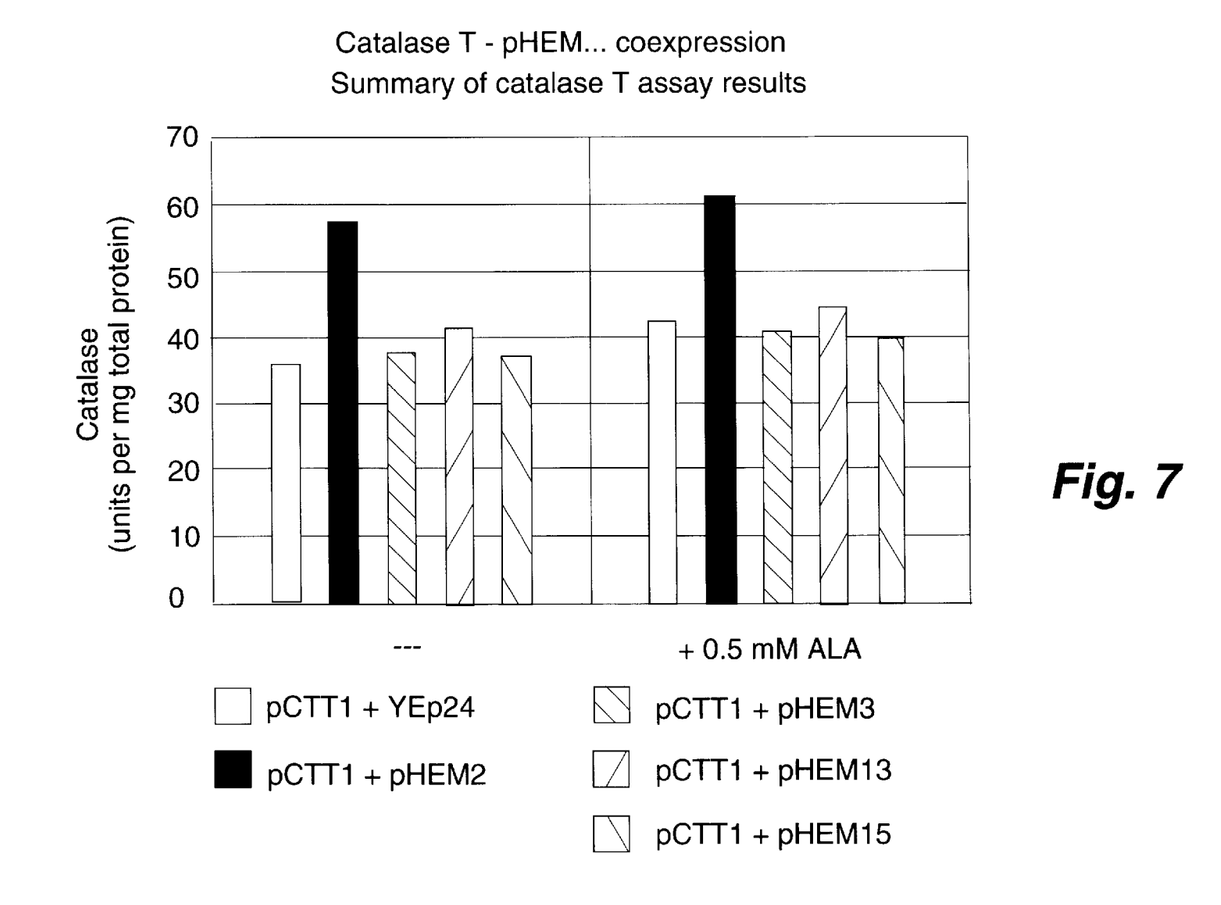
FIG. 7 shows the results of catalase assays in a series of double transformant yeast cultures simultaneously harboring the multicopy plasmid pCTT1 and one of the following multicopy plasmids: pHEM2, pHEM3, pHEM13, and pHEM15.

Use of the catalase T gene also provides what can be termed a "trap" for excess heme that is produced as a result of increasing the amount of a rate-limiting enzyme in a heme biosynthetic pathway. FIG. 2 is a restriction and functional map of the catalase T gene and its product. For example, in yeast the rate-limiting enzyme is encoded by HEM2. By transforming yeast cells with CTTI to produce catalase T, the catalase T is overexpressed and is capable of complexing with excess heme produced by a host cell that overproducing heme. By trapping excess heme with catalase T apoprotein, negative feedback caused by accumulation of free heme is reduced or eliminated. The results of 5-ALA dehydralase and catalase assays in double transformant yeast cells simultaneously harboring the multicopy plasmids pCTT1 and pHEM2, are shown in FIG. 6. FIG. 7 shows the results of catalase assays in a series of double transformant yeast cultures simultaneously harboring the multicopy plasmit pCTT1 and one of the following multicopy plasmids: pHEM2, pHEM3, pHEM13, and pHEM15. The experimental conditions for experiments as depicted in FIGS. 6 and 7 entail selection double transformants in a minimal medium lacking lucine (selection for pCTT1) and uracil (selection of any of the pHEM plasmids). Two 100 milliliter cultures were grown in shake flasks to a density of A-600≈2.5 followed by harvesting (centrifugation, washing etc.) cellysis by freezing-thawing in liquid nitrogen. A catalase T assay was performed using standard known procedures.

The great advantage of using catalase is that is an enzyme, and as such, can be readily measured by virtue of its extremely active catalytic destruction of hydrogen peroxide. This high sensitivity allows the easy measurement of very small changes in the levels of catalase formation and thus, indirectly, in the intracellular heme concentration. The use of catalase as a trap for heme also permits researchers to investigate other factors, such as the effective flux through the heme pathway, including heme transport proteins, etc., without interference from heme feedback inhibition. The use of the catalase T gene to transform cells, therefore, serves as a model for expression in yeast of heterologous genes, including human hemoglobin genes. Because catalase, being an enzyme, is more benign than hemoglobin to a cell, apocatalase can bind to excess heme found in the cell so that the heme does not shut down various biosynthetic pathways. It is preferred to have promoters, whether inducible or constitutive, for both a catalase T gene as well as the HEM2 gene so as to coordinate appropriate amounts of each constituent, thereby precluding the possibility of feedback inhibition by free heme and to provide simultaneous abundant amounts of such constituents.

An important aspect of the present invention is the simultaneous production of a sufficient amount of desired apoproteins and heme so that efficient production of desired amounts of hemoproteins can be achieved. Without simultaneously available abundant amounts of both apoprotein and heme constituents, improper folding of apoproteins, and thus non-functional hemoproteins, can be created. By providing a method to simultaneously generate abundant amounts of both apoprotein and heme, the present method provides a production system where functional, properly folded hemoproteins are produced in a cell and heme-feedback inhibition of the pathway is avoided. In other words, an appropriate ratio of apoproteins and heme are simultaneously produced by using the present method to permit desired production of functional hemoproteins in unprecedented quantities. By achieving such ratios, heme feedback inhibition is of little consequence and further investigation of other important elements of the biosynthetic pathways within a cell can be further pursued. Using the present invention, the amount of hemoproteins produced by any given hemoprotein producing cell can be increased by up to about 20%, more preferably up to about 30%, and most preferably up to about 40% of hemoprotein concentration, as compared to control cells.

The present inventors have determined the nucleotide sequence of a 1890 base pair DNA fragment containing the HEM2 promoter and upstream flanking sequences (see FIG. 3). This DNA fragment was cloned into the vector pGEM7Zf+ (Promega, Madison, Wis.) as a 1.7 kD BamHI-HindIII fragment and the DNA sequence was determined in a series of nested-deletion sub-clones using the di-deoxy chain termination technique (Asubel et al., 1989). The nucleic acid sequence of an 1895 base pair DNA fragment which includes an 1889 base pair fragment containing the HEM2 promoter and upstream flanking sequences and a 6 base pair fragment containing the HEM2 start codon and the next three bases of the HEM2 coding region, is represented herein as SEQ ID NO:1. The sequencing of the start codon proximal 180 BPA confirmed a previously published portion of the sequence (Myers et al., 1989). The HEM2 promoter sequence was analyzed for the presence of restriction and nuclease recognition sites as well as for various punitive regulatory elements. The HEM2 promoter sequence has been assigned GenBank Accession No. L22937.

The present inventors are the first to appreciate that the expression of HEM2 in yeast may be regulated, not only by its carbon source, but also by heme in combination with a set of general transcriptional regulators. (Heme is also known to regulate ALA-S production (encoded by HEM 1)). This is confirmed by the significant match between the published consensus regulatory sequences (see Verdier, 1990) with the potential regulatory sites indicated in FIG. 3.

One aspect of the present invention relates to a vector host system for recombinant hemoprotein production, and in particular, hemoglobin production. In one embodiment, *Pichia pastoris* vectors are used. Although the yeast *Saccharomyces cerevisiae* can be used, as well as several other yeast strains, preferred yeast strains include *Pichia pastoris* and *Hansenula polymorpha* due to their exceptionally high yields. In one embodiment of the present invention, a Pichia strain is used in cytochrome and catalase production. Using such Pichia strains, increased levels of hemoprotein production can be achieved, including over-expression of genes in the hemoglobin synthetic pathway.

The present invention therefore provides a superior alternative to existing bacterial systems for the production of hemoproteins, such as hemoglobin, and additionally, provides a system for the analysis of structure-activity relationships in the production of hemoproteins. The present invention provides the means for designing experiments to further investigate the interrelationships between heme concentration and various interactions between components involved in heme protein synthesis. By the teachings contained herein, one of skill in the art is taught how to make and use host cells to increase the production of desired hemoproteins, such as hemoglobin, which is suitable for development of hemoglobin-based red blood cell substitutes.

While various embodiments of the present invention have been described in detail, it is apparent that modifications and adaptations of those embodiments will occur to those skilled in the art. It is to be expressly understood, however, that such modifications and adaptations are within the scope of the present invention, as set forth in the following claims.

What is claimed is:

1. A method of expressing a hemoprotein, comprising:
    transforming a host cell with a nucleic acid sequence encoding a rate-limiting enzyme in a heme biosynthetic pathway;
    culturing said host cell under conditions effective to provide expression of said sequence to produce a desired concentration of heme; and
    expressing a sufficient amount of a heme-binding apoprotein of said hemoprotein, which apoprotein complexes with heme produced by said cell, to reduce the concentration of free heme within said cells thereby resulting in the expression of said hemoprotein.

2. The method as set forth in claim 1, wherein said nucleic acid sequence comprises a HEM2 gene.

3. The method as set forth in claim 2, wherein said expression of said HEM2 gene is controlled by a constitutive yeast promoter.

4. The method as set forth in claim 1, wherein said hemoprotein comprises hemoglobin.

5. The method as set forth in claim 1, wherein said host cell is a yeast cell.

6. The method as set forth in claim 5, wherein said yeast cell is selected from the group consisting of yeast cells of the genus Pichia and Hansenula.

7. The method as set forth in claim 1, wherein said host cell is a filamentous fungus cell.

8. The method as set forth in claim 7, wherein said fungus cell is selected from the group consisting of fungus cells of the genus Aspergillus and Neurospora.

9. The method as set forth in claim 1, further comprising transforming said host cell with a nucleic acid sequence encoding a protein that facilitates secretion of said hemoprotein.

10. The method of claim 1, wherein said hemoprotein is heterologous with respect to said host cell.

11. The method as set forth in claim 1, wherein said heme-binding apoprotein comprises a catalase T apoprotein.

12. The method of claim 1, wherein said heme binding apoprotein is an apoprotein of an enzyme.

13. The method of claim 1, wherein said heme binding apoprotein is selected from the group consisting of the apoproteins of hemoglobin, myoglobin and cytochrome P450.

14. A method for expressing a hemoprotein, comprising:
    transforming a host cell with a vector comprising multiple copies of a HEM2 gene;
    culturing said host cell under conditions effective to provide expression of said vector to produce a desired concentration of heme; and
    expressing a sufficient amount of a heme-binding apoprotein of said hemoprotein, which apoprotein complexes with heme produced by said cell, to reduce the concentration of free heme within said cell, thereby resulting in the expression of said hemoprotein.

15. A method for expressing enhanced levels of a heterologous hemoprotein in a yeast cell, comprising:
    transforming said yeast cell with at least one HEM2 nucleic acid sequence;
    culturing said yeast cell under conditions wherein said HEM2 nucleic acid sequence is expressed;
    reducing the concentration of free heme produced by said cell to prevent negative feedback inhibition caused by accumulation of free heme within said cell by expressing a heme-binding apoprotein of said hemoprotein, thereby resulting in the enhanced expression of said heterologous hemoprotein.

16. A method for increasing the expression of a desired hemoprotein, comprising:
coordinating the production of a desired apoprotein of said hemoprotein with the production of heme by:
(1) overexpressing a rate-limiting enzyme in the heme biosynthetic pathway within a cell; and
(2) reducing the amount of free heme within said cell by overexpressing said apoprotein and complexing free heme with said apoprotein so as to reduce feedback inhibition by heme, thereby resulting in the increased expression of said hemoprotein.

* * * * *

SEQUENCE LISTING ( 1 ) GENERAL INFORMATION:

( i i i ) NUMBER OF SEQUENCES: 1

( 2 ) INFORMATION FOR SEQ ID NO:1:

( i ) SEQUENCE CHARACTERISTICS:
( A ) LENGTH: 1895 base pairs
( B ) TYPE: nucleic acid
( C ) STRANDEDNESS: single
( D ) TOPOLOGY: linear ( i i ) MOLECULE TYPE: DNA (genomic)

( x i ) SEQUENCE DESCRIPTION: SEQ ID NO:1:

```
GGATCCAATC  ATTCCTGTTC  GATAATCTCA  AAGGGACATT  CCCCTCTGGA  GAGAAATTAG      60

TGACAAAGCT  GTGGTCAGTT  GGATAAGAGT  TCTCTTGTAC  CCCTTGTGAC  GAGAATAAAA     120

TAACAAAAAA  AAATGCAAAC  AGCAAACGAC  AAGCACAAGC  ACAATATAGC  TTATAAGGCC     180

ATTCCTAGCA  ATTTTCGGAA  GAATGGCTAT  ACCCAAATAC  AGATTTGGCG  ACAGTTTACA     240

CATGGAGATG  CGACATCGTG  CTCTATTGGA  TAAAGTCAAA  TCATCCCTAT  ATTATCTATC     300

CCTGTCATAT  GCTGCGAGTA  TCCGTTAAAG  TCAACCTGTG  CATTCTTTGC  TGACATTCAG     360

TATACCATCA  ACGGCATCAT  TCCCCCTTGC  TCCAGTCGGG  TTCCGTCATA  AACATTTATC     420

TGCCCTTTCC  AGTCATTTGT  TCCTGACAGA  GAAACTGTCC  CTCTGTTTAC  ATTTATGACA     480

GTGTCTGCAC  ATGAACCGGA  ATCCATACGG  GTGAAATTAG  TTGAGAGTGT  ATAGCCATTA     540

ACACCATCAA  AATTTACTTC  CGCATAACCA  TCTCCTGCTC  CCATAGATAC  AGGATTGAAC     600

TGTCATGTGC  AGAGATCGAC  ACTCGTCAGT  ATCAACTCTA  CGCGCACTGT  GTAAATCATT     660

AGAATGTAAC  CAGGTTCCGT  GAGATTTCTT  ATATATGACT  ACGAGACAGT  GCTTTCAGAC     720

GCAAAGTCTA  ACCATCCTTG  AAAACGTCTT  CCAATCATGA  AATTAAAACT  CACGGCTCTA     780

TATTTTCACG  TCGAGCTTCA  TTTTGGGCCA  CTATTAGATC  CTGTGTTTTT  ATTCCAAGGT     840
```

```
GTATTGTCAT   ATTTAATCTT   GAAAATAATT   TCTAATCTGT   GTGATTATTA   CAGTAGATTC        900

TATTGAAAGG   ACACCTACAA   GCTCATAGAG   TCCGGTGTAC   TGGCACAGAA   CACAGATGAC        960

AATACAAAAG   TAAATAAATC   TATCGACAGC   AATTCCTATT   TTCTTTTACA   TTTATATTGA       1020

TTAGCTTACG   ATTTCTGTAT   TTATAGAGCG   TGTAGTTACA   TATCCAGATA   CCTGTCTTCT       1080

AGGTGAACAG   TTGGTTTCAG   TCAAAAATTA   TTATTACGGA   TTCTTGGACG   GTAGCTTTCC       1140

TGCCTGCATG   ATTCCACTCT   TTCGGGAACA   ATGATAATTA   TTGTTAGTTT   TGATTATGCT       1200

TAATCTTAAT   TCGCACATGG   AATGCCTGCA   TTGTCACGAG   AACATTGAAA   CATATACAAA       1260

AAACAAATTT   GAAATAGAAA   ACAAAGCAAT   TTACAGAAAT   GACTGCCTGG   TGCTAATTCT       1320

TGCATATATT   TTATTTTTAA   TTAACTAGAA   ATCAGCGTCA   ATTATAGTTT   CTGGTGAGTC       1380

AGCCAATGTC   TGTAAATAAA   AACAATATGC   TTAAGAGGAT   TAACAGTGGC   ACAAGAGGCA       1440

AAGAAGGGAA   GAAGGCGTAC   ACGTCACATG   AATATATAAA   AAGGAGTGTT   ACTATCAATT       1500

GGACCATCTT   CGACGTTTCT   ATCTGCTACA   AGCCTGTGTC   GCCGAATTAC   TTTATTGGGT       1560

CTTGTATATA   CGCCGAAATA   CATCATCATT   CCAAGATCGA   CGATAAAATC   ATCCAAAAAA       1620

TTGTTGCCGA   AAAAAAAATT   GGAAAAGGTG   AAAAAAAAAT   CAAAATACGG   GTAAACGAGC       1680

AATCCCTGTT   CGGTGCGGTG   ATTGGCTTGA   GGCAAGCTTC   CCGCTTGATT   TATATAAGAG       1740

TAAGGCAACC   TAATAAATGC   TAGCAACATC   TATCGCCCAC   TCTATTGTCT   TTGATTTTCT       1800

TGCCCAATCA   GCCAAATAAA   AAAAGTTTT    ACTGCTTACT   CATATTATTG   CTTACTCCAG       1860

TAATTCATAC   CTAGAAAATT   GACAAAACCA   TGCAT                                      1895
```